(12) United States Patent
Ueno

(10) Patent No.: US 7,126,116 B2
(45) Date of Patent: Oct. 24, 2006

(54) MASS SPECTROMETER

(75) Inventor: Yoshihiro Ueno, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 11/075,671

(22) Filed: Mar. 10, 2005

(65) Prior Publication Data
US 2005/0199802 A1 Sep. 15, 2005

(30) Foreign Application Priority Data
Mar. 11, 2004 (JP) .............................. 2004-068363

(51) Int. Cl.
*B01D 59/44* (2006.01)
(52) U.S. Cl. .................................................... 250/290
(58) Field of Classification Search ................. 250/290
See application file for complete search history.

(56) References Cited

U.S. PATENT DOCUMENTS 5,598,001 A * 1/1997 Flory et al. ................. 250/292
5,998,787 A * 12/1999 Hager ......................... 250/282

FOREIGN PATENT DOCUMENTS

JP 2000-149865 5/2000
JP 2002-228637 8/2002

* cited by examiner

*Primary Examiner*—Jack Berman
*Assistant Examiner*—Jennifer Yantorno
(74) *Attorney, Agent, or Firm*—Westerman, Hattori, Daniels & Adrian, LLP.

(57) ABSTRACT

A mass spectrometer includes: an ion source; a mass separator for separating ions with respect to mass to charge ratios of the ions; an ion detector; an ion deflector including a pair of electrodes placed opposite each other across an ion optical axis, the ion deflector being placed between the ion source and the mass separator or between the mass separator and the ion detector; and a voltage generator for applying AC voltages of opposite polarities respectively to the pair of electrodes, where a frequency of the AC voltages is determined so that lighter ions are more deflected and prevented from entering the mass separator or the ion detector and heavier ions are less deflected and allowed to enter the mass separator or the ion detector. Only helium ions which are deleterious to the mass spectrometry can be efficiently eliminated while object sample ions are hardly affected. This enables a high-sensitivity and high-accuracy mass analysis of ions whose mass to charge ratios are close to that of helium ions, which until now has been difficult.

5 Claims, 5 Drawing Sheets

Fig. 3
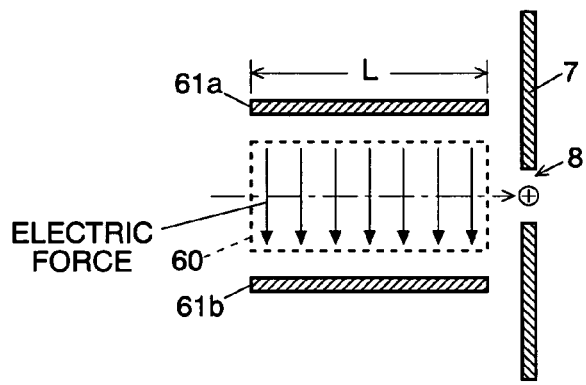
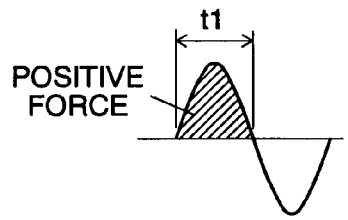
Fig. 4A
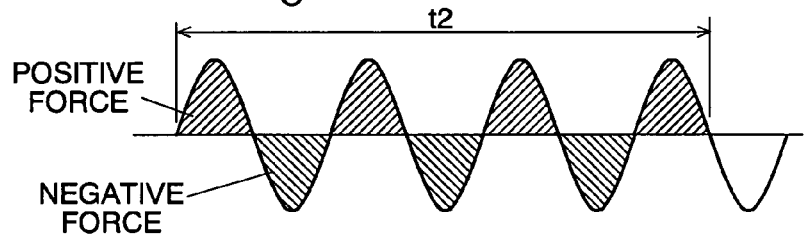
Fig. 4B
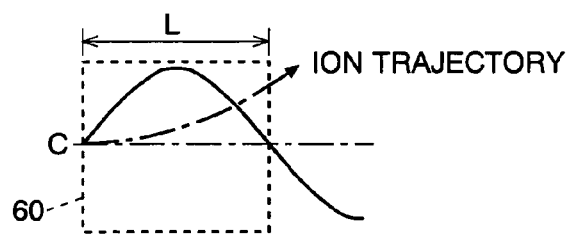
Fig. 5A
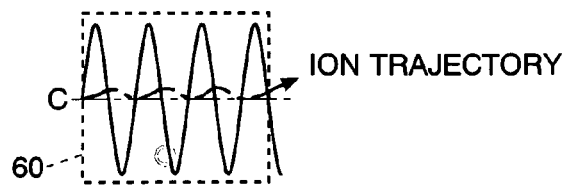
Fig. 5B

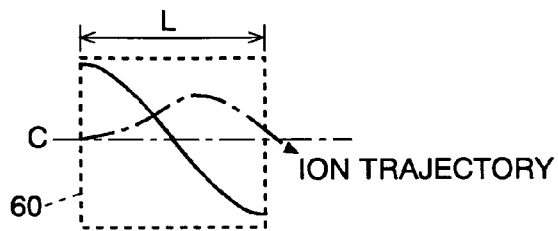
Fig. 6
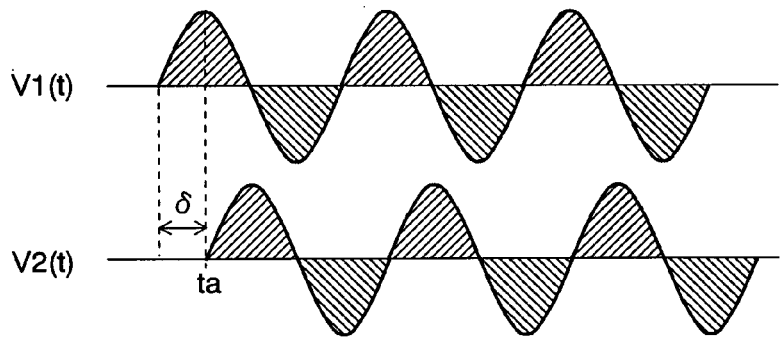
Fig. 7
Fig. 8A
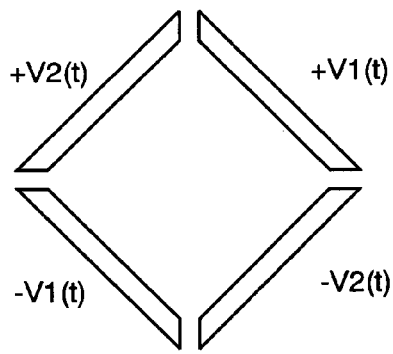
Fig. 8B
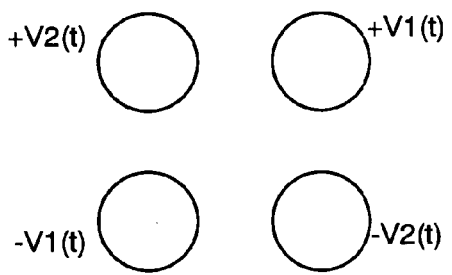
Fig. 8C
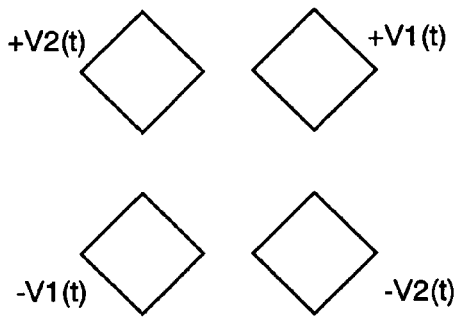

MASS SPECTROMETER

The present invention relates to a mass spectrometer, especially to one suitable as a detector for a gas chromatograph.

BACKGROUND OF THE INVENTION

A mass spectrometer is often used with a gas chromatograph or a liquid chromatograph. When used with a gas chromatograph, the mass spectrometer is used as the detector. In such a gas chromatograph, a sample containing plural components is made to pass through a gas chromatograph column, where the components are separated with respect to time while the sample passes through the column, and every one of the separated components is introduced via an interface to the mass spectrometer. In the interface, molecules of the component gas are ionized, and the ions are separated by the mass spectrometer with respect to their mass to charge ratios.

In the gas chromatograph section, the sample gas is carried by a carrier gas in the column, and a separator is provided in the interface to separate the carrier gas from the sample, as described in paragraph [0003] and FIG. 8 of the Japanese Unexamined Patent Publication No. 2002-228637. For the carrier gas, the helium gas is normally used. Since the amount of carrier gas is far greater than that of the sample gas, the carrier gas cannot be completely separated, and some part of it reaches an ionizer of the mass spectrometer, where the amount of the carrier gas reaching the ionizer is still far greater than that of component gases of the sample. Though normally it is difficult to ionize the helium gas, it can be ionized when the electron accelerating voltage is raised to increase the ion producing efficiency in the electron impact (EI) ionization method.

Since, as described above, the amount of the carrier helium gas reaching the ionizer is far greater than that of the components of the sample, the amount of ionized carrier helium gas is still larger than that of the sample component ions, so that the detection signal of the sample components is hidden by the detection signal of, or noise by, the carrier helium ions if no measures are taken. The problem is apparent when light elements (for example, lithium, beryllium, boron, etc.) having masses close to helium are to be analyzed. Though it is possible to suppress ionization of helium atoms by decreasing the electron accelerating voltage in the ionizer, the production of ions of sample components is also suppressed and the sensitivity of the mass analysis deteriorates. This makes the analysis of minute (or trace) components difficult.

When ions having mass to charge ratios far larger than that of helium ions are analyzed, they are adequately separated from the helium ions by a mass separator such as the quadrupole mass filter, and the detection signal of such heavy ions would not be hidden by the detection signal (or noise) of helium ions. But the amount of helium ions is so large that, even if the fraction of helium ions passing through the mass separator is small, the number of helium ions entering the detector is still large compared to that of the sample ions. This makes a considerable background noise in the detection of object ions.

Neutral particles such as helium atoms (molecules) are conventionally eliminated by an ion optical system placed before the mass separator. In the mass spectrometer described in the Japanese Unexamined Patent Publication No. 2000-149865 (which has matured to patent No. 3379485), the outlet axis of the heated capillary and the inlet axis of the subsequent skimmer are designed to be displaced: ions are guided from the exit of the heated capillary to the entrance of the skimmer by an electric field formed by an ion optical system provided between them, while neutral particles are not affected by the electric field and cannot enter the skimmer. This method is not effective when helium gas atoms (molecules) are ionized.

SUMMARY OF THE INVENTION

An object of the present invention is therefore to provide a mass spectrometer in which carrier helium ions are adequately eliminated before they enter the mass separator, whereby ions having masses close to helium ions can be analyzed, and sensitivity and accuracy of the mass spectrometer are enhanced with less background noises.

According to the present invention, a mass spectrometer includes:

an ion source;

a mass separator for separating ions with respect to mass to charge ratios of the ions;

an ion detector;

an ion deflector including a pair of electrodes placed opposite each other across an ion optical axis, the ion deflector being placed between the ion source and the mass separator or between the mass separator and the ion detector; and a voltage generator for applying AC voltages of opposite polarities respectively to the pair of electrodes, where a frequency of the AC voltages is determined so that lighter ions are more deflected and prevented from entering the mass separator or the ion detector and heavier ions are less deflected and allowed to enter the mass separator or the ion detector.

Since the kinetic energy of an ion generated in the ion source does not depend on its mass to charge ratio, and its speed is inversely proportional to the square root of the mass to charge ratio, ions of smaller mass to charge ratios have higher speed. In the mass spectrometer of the present invention, ions of smaller mass to charge ratios enter the ion deflector at higher speed, and ions of larger mass to charge ratios enter it at a lower speed. Thus ions of smaller mass to charge ratios pass through the ion deflector in a shorter time period, and ions of larger mass to charge ratios pass through it in a longer time period. Accordingly, the number of cycles (waves) of the AC voltage generated in the ion deflector while ions of smaller mass to charge ratios pass through the ion deflector is small, and that while ions of larger mass to charge ratios pass through it is large.

Since an ion has an electric charge, the electric field generated by the AC voltage applied to the electrodes in the ion deflector exerts a force to the ion, and the direction of the force acting on the ion changes alternately, which will be referred to as the positive direction and the negative direction, every half cycle of the AC voltage. If the number of cycles of the AC voltage generated while an ion passes through the deflector is smaller than one, or preferably smaller than a half, the force of either one of the two directions exceeds the other, and the ion is deflected according to the prevailing force. If, on the other hand, the number of cycles of the AC voltage is larger than one, or preferably larger than two, both the positive force and the negative force arise while an ion passes through the ion deflector, and the two forces acting on an ion tend to cancel each other out, so that the ion is less deflected. Thus, by appropriately determining the frequency of the AC voltage applied to the pair of electrodes in the ion deflector, ions of smaller mass to charge ratios are deflected and eliminated, while ions of larger mass to charge ratios are unaffected and go to the subsequent mass separator (or ion detector).

The ion deflector of the present invention is thus capable of eliminating ions having mass to charge ratios smaller than a desired value. But, since the mass separator also has the function of separating ions by their mass to charge ratios, the ion eliminating function of the present invention is effective to such ions whose amount is too large to eliminate in the mass separator. Specifically, the mass spectrometer of the present invention is effective in eliminating the undesirable helium ions generated from the helium gas as the carrier gas of a gas chromatograph mass spectrometer.

In the mass spectrometer of the present invention, only helium ions which are deleterious to the mass spectrometry can be efficiently eliminated while object sample ions are hardly affected. This enables a high-sensitivity and high-accuracy mass analysis of ions whose mass to charge ratios are close to that of helium ions, which until now has been difficult. And the background noise due to carrier gas helium ions is adequately suppressed, which enables the improvements in the sensitivity and accuracy of the mass analysis in general.

BRIEF DESCRIPTION OF THE DRAWINGS

FIG. 3 is a longitudinal cross-sectional view of deflecting electrodes for explaining the force acting on an ion passing through the deflecting electrodes.

FIG. 4A is a graph of a wave of the AC voltage generated in the case of ions of smaller mass to charge ratios, and FIG. 4B is the same in the case of ions of larger mass to charge ratios, where both graphs have the abscissa of time.

FIG. 5A is a graph of a wave of the AC voltage generated in the case of ions of smaller mass to charge ratios, and FIG. 5B is the same in the case of ions of larger mass to charge ratios, where both graphs have the abscissa of space.

FIG. 6 shows waveforms of the AC voltage at different timings in the time period while an ion passes through the deflecting electrodes.

FIG. 7 is a comparison of the waveforms of two AC voltages V1(t) and V2(t) having a difference in the phase.

FIGS. 8A–8C show examples of the deflecting electrodes including two pairs of electrodes.

DETAILED DESCRIPTION OF A PREFERRED EMBODIMENT

Figure 1:
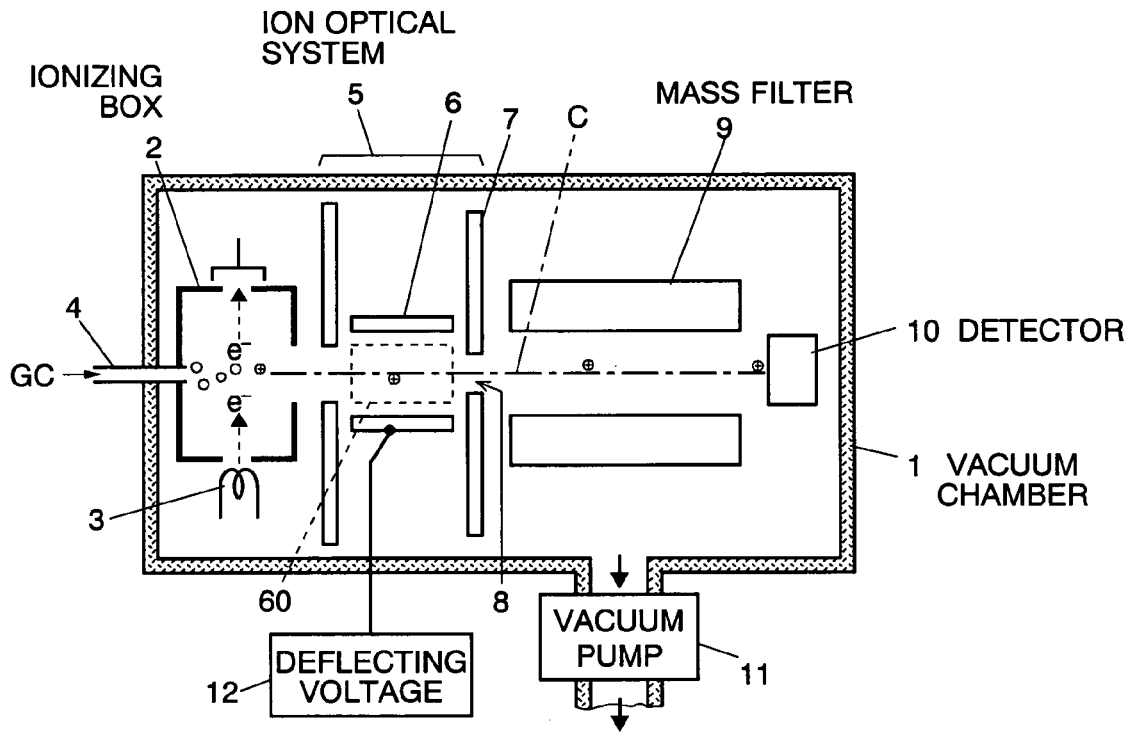
FIG. 1 is a schematic diagram of a mass spectrometer embodying the present invention.

A mass spectrometer embodying the present invention is described. As shown in FIG. 1, an ionizing box 2, an ion optical system 5, a quadrupole mass filter 9 and an ion detector 10 are aligned on an ion optical axis C in a vacuum chamber 1, which is evacuated by a vacuum pump 11. The ionizing box 2 and the quadrupole mass filter 9 respectively correspond to the ion source and the mass separator of the present invention. The ion optical system 5, which accelerates and converges ions as normal ones do, includes deflecting electrodes 6 which correspond to the ion deflector of the present invention.

Though not shown in the drawing, a gas chromatograph is connected before the mass spectrometer of the present invention, wherein, in the gas chromatograph, a sample gas carried by a carrier gas flowing out of a separation column of the gas chromatograph is supplied to the ionizing box 2 through an appropriate interface. In the ionizing box 2, molecules or atoms of the sample gas are ionized by the EI method as follows. Thermal electrons generated by a heated filament 3 are accelerated by an appropriate voltage applied between the filament 3 and a cathode placed across the ionizing box 2. The electrons are injected into the ionizing box 2, and contact the sample molecules or atoms, which are ionized by the electrons.

Thus generated ions are drawn out of the ionizing box 2, and introduced through the ion optical system 5 to the central longitudinal space of the quadrupole mass filter 9. An appropriate combination of a DC voltage and an AC voltage is applied to the rods of the quadrupole mass filter 9, so that ions having a specific mass to charge ratio (m/z) corresponding to the applied voltage can pass through the longitudinal space of the quadrupole mass filter 9 and detected by the ion detector 10, while other ions dissipate from the space and do not enter the ion detector 10.

In addition to the sample molecules or atoms, molecules (or atoms) of carrier helium gas enter the ionizing box 2 in a large amount, and are also ionized. If the mass to charge ratio of the sample ions is large enough compared to that of the helium ions, a large portion of the helium ions is eliminated in the quadrupole mass filter 9. Since, however, the whole amount of carrier helium gas is very large, a lot of helium ions, though small compared to the whole amount, enter the ion detector 10, which constitutes background noises. If the mass to charge ratio of the sample ions, e.g., lithium, beryllium, or boron ions, is close to that of the helium ions, they are difficult to separate in the quadrupole mass filter 9. In this case, a lot of unwanted carrier gas ions enter the ion detector 10 together with the sample ions, and the detection signal of the sample ions are hidden by the detection signal (or noise) of those ions.

In the mass spectrometer of the present embodiment, helium ions, which are lightweight, are eliminated from the quadrupole mass filter 9 by the deflecting electric field 60 generated by the deflecting electrodes 6 and a rear end electrode 7 placed after the deflecting electrode 6, where the rear end electrode 7 has an aperture 8 through which only sample ions are allowed to pass to the quadrupole mass filter 9.

Figure 2:
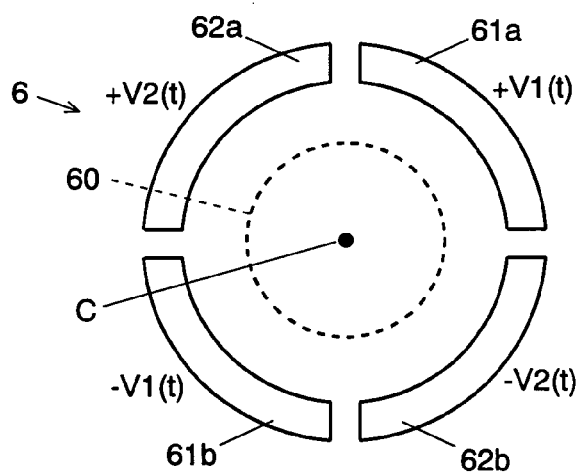
FIG. 2 is a cross-sectional view of deflecting electrodes on the plane perpendicular to the ion optical axis C of the mass spectrometer.

As shown in FIG. 2, which is a cross-sectional view of the deflecting electrodes 6 on the plane perpendicular to the ion optical axis C, the deflecting electrodes 6 are made of four pieces of quarter-cylindrical electrodes symmetrically arranged around the ion optical axis C. The two electrodes 61a and 61b placed opposite each other across the ion optical axis C make a pair, and the other two electrodes 62a and 62b also placed opposite each other across the ion optical axis C make another pair. A deflecting voltage generator 12 applies voltages of opposite polarities to the two electrodes of each pair: i.e., the voltage +V1(t) is applied to the electrode 61a, the voltage −V1(t) is applied to the other electrode 61b of the same pair, the voltage +V2(t)

is applied to the electrode 62*a*, and the voltage −V2(t) is applied to the other electrode 62*b* of the same pair. Specifically, the voltages V1(t) and V2(t) are $$V1(t)=V0+Va\cdot\sin \omega t, \text{ and}$$

$$V2(t)=V0+Vb\cdot\sin(\omega t+d).$$

As seen in the above equations, the voltages V1(t) and V2(t) are both made of the same DC voltage V0 plus AC voltages having different amplitudes Va, Vb and the same frequency ω with a difference in the phase by d.

The process in which helium ions are eliminated by the deflecting electric field 60 is described using FIGS. 3–5. For simplicity of explanation, it is supposed here that the deflecting electric field 60 is generated solely by applying AC voltages of opposite polarities (or voltages of the same amplitude and same frequency but with the phases shifted by 180°) to the two opposing electrodes 61*a* and 61*b*, as shown in FIG. 3.

The initial kinetic energy of an ion accelerated by the voltage V is calculated by the equation $$z\cdot e\cdot V=(\tfrac{1}{2})\cdot m\cdot v^2,$$

where z is the charge number of the ion, e is the charge of an electron, and v is the speed of the ion. The above equation is rewritten as $$e\cdot V=(\tfrac{1}{2})\cdot(m/z)\cdot v^2,$$

which shows that the speed v of an ion is inversely proportional to the square root of the mass to charge ratio m/z of the ion if the accelerating voltage V is kept constant. This means that ions of smaller mass to charge ratios gain higher speed when accelerated by the same voltage.

Since, as shown in FIG. 3, the length L of the deflecting electric field 60 is fixed, lighter ions having a higher speed pass through the deflecting electric field 60 in a shorter time, and heavier ions having a smaller speed pass through it in a longer time. Because helium is the lightest element bar hydrogen, the time t1 for a helium ion to pass through the deflecting electric field 60 is shorter than the time t2 for heavier ions to do the same (t1<t2). The difference in the passing time is larger as the difference in the mass of the ions is larger. Since the frequency ω of the AC voltage generating the deflecting electric field 60 is fixed, the number of waves of the AC voltage while an ion passes through the deflecting electric field 60 is smaller for lighter ions and larger for heavier ions.

FIGS. 4A and 4B schematically show the waves of the AC voltage generated while an ion passes through the deflecting electric field 60, where the abscissa is time. FIGS. 5A and 5B schematically show the waves of the AC voltage generated while an ion passes through the deflecting electric field 60, where the abscissa is space. It is supposed that, as shown in FIGS. 4A and 5A, the AC voltage wave is generated for 0.5 cycles within a time period of t1 in which a helium ion passes through the space between the deflecting electrodes 6, and that, as shown in FIGS. 4B and 5B, the AC voltage wave is generated for 3.5 cycles within a time period of t2 in which a sample ion heavier than a helium ion passes through the same. In the first half of a cycle (i.e., within the phase angle of 0–180°) of the AC voltage, a downward force (which is referred to as the positive force) is exerted on an ion, as shown by the arrows in FIG. 3, and in the last half of a cycle (i.e., within the phase angle of 180–360°), an upward force (negative force) is exerted to an ion.

In the case of FIGS. 4A and 5A, ions undergo only positive force while they pass through the space between the deflecting electrodes 6, so that their course is deflected and they cannot pass through the aperture 8 but collide with the rear end electrode 7. In the case of FIGS. 4B and 5B, on the other hand, ions undergo the positive force and negative force alternately, and the both forces cancel each other (the last 0.5 cycles is negligible in this case). Thus ions do not deflect from the ion optical axis C, and can pass through the aperture 8. This enables separating ions of different mass to charge ratios: ions of smaller mass to charge ratios, including helium ions, are deflected and eliminated, and object ions or ions of larger mass to charge ratios can be passed to the subsequent quadrupole mass filter.

As can be easily understood by the above explanation, how many waves arise within the time period while an object ion passes through the space between the deflecting electrodes 6 is critical in separating object ions and unwanted carrier ions with the deflecting electric field 60. Since an ion has a momentum, its movement in the space between the deflecting electrodes 6 does not fully accord with the AC voltage applied to the deflecting electrodes 6. Thus, in general, the lateral movement of an ion is smaller and the ion will more probably pass through the aperture 8 as the number of waves (or cycles) of the AC voltage is larger while the ion passes through the space between the deflecting electrodes 6. In principle, a proper elimination of unwanted carrier ions is possible if the frequency of the AC voltage is determined so that the number of waves (cycles) generated within the time period t1 while a helium ion passes through the space between the deflecting electrode 6 is less than one, and the number of waves generated within the time period t2 while an object sample ion passes through the same is more than one.

The eliminating efficiency of the helium ions is lower as the number of waves generated within the time period t1 is closer to one, and the passing efficiency of the object sample ions is lower as the number of waves generated within the time period t2 is closer to one. It is preferable, in practice, to set the number of waves at less than 0.8, more preferably at less than 0.5. Among ions whose corresponding number of waves is larger than one in the time period t2, ions that can pass through the aperture 8 with efficiency higher than a certain level are analyzed.

The deflecting electrode 6 should have the length L longer than a certain level. If the length L is too small, the deflection of unwanted ions is not large enough and the ions pass through the aperture 8 even if the positive or negative force is exerted to the ions.

In the above description, the phase angle of the AC voltage at the time a helium ion enters the space between the deflecting electrodes 6 is supposed to be zero, as shown in FIG. 5A. Actually, however, the phase angle depends on the time when a helium ion enters the deflecting electrodes 6. If the phase angle at the time a helium ion enters the deflecting electrodes 6 is about 90°, the waveform of the AC voltage in the time period t1 while it passes through the space between the deflecting electrodes 6 is as shown in FIG. 6. In this case, the positive force and the negative force acting on the helium ion almost cancel each other, so that the helium ion does not deviate from the ion optical axis C, and may pass through the aperture 8.

In order to avoid such a case happening, as already shown in FIG. 2, two sets (or two pairs) of the deflecting electrodes may be provided. In this case, the voltages V1(t) and V2(t) respectively applied to the two pairs of deflecting electrodes (61*a*, 61*b*), (62*a*, 62*b*) have the AC components of the same frequency but differ in the phase angle by δ (the amplitudes of the two AC voltages V1(t) and V2(t) can be different). The difference in the phase angle δ is set at 90° (or a quarter cycle), as shown in FIG. 7. Owing to the two sets (or pairs) of deflecting electrodes (61a, 61b), (62a, 62b), two sets of electric fields are generated between the deflecting electrodes 6, where the two electric fields are perpendicular to each other, so that either or both electric fields necessarily deflect the ion.

If a helium ion enters the space between the deflecting electrodes 6 at the time ta when the phase angle of the voltage V1(t) is 90°, as shown in FIG. 7, the positive and negative forces acting on the ion almost cancel each other, and the ion does not deflect from the ion optical axis C. But, due to the electric field generated by the other voltage V2(t), whose phase angle differs from that of the voltage V1(t), only positive force acts on the ion. The force deflects the ion from the ion optical axis C, and the ion is prevented by the rear end electrode 7. Thus, by providing two electric fields with different phase angles, a helium ion entering the space between the deflecting electrodes is deflected by either of the electric fields, and is prevented from passing through the aperture 8 with high probability.

The deflecting electrodes 6 are not limited to those shown in FIG. 2, but can be any shape if two pairs of electrodes are provided across the ion optical axis C. Some examples are shown in FIGS. 8A–8C: the deflecting electrodes of FIG. 8A are made of parallel plates, those of FIG. 8B are made of circular rods (or hollow pipes), and those of FIG. 8C are made of square rods (or hollow pipes).

Figure 9A:
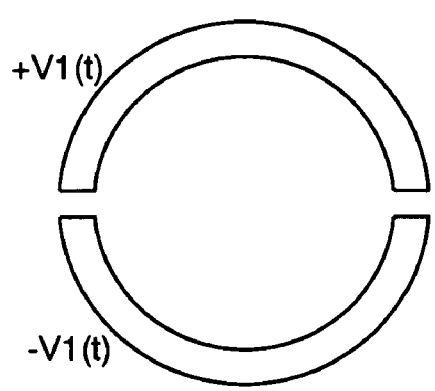
FIGS. 9A and 9B show examples of the deflecting electrodes including a single pair of electrodes.
Figure 9B:
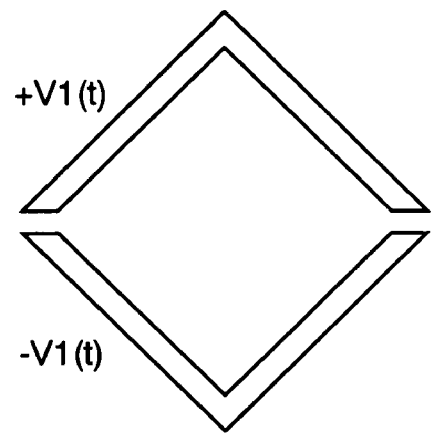

The deflector may be more different if it can control the timing of a helium ion entering it, or, more specifically, if a helium ion enters it at the time when the positive force and negative force acting on the helium ion do not cancel. It is further possible to use a single pair of electrodes as the deflector if such a condition is satisfied, as shown in FIGS. 9A or 9B.

Figure 10:
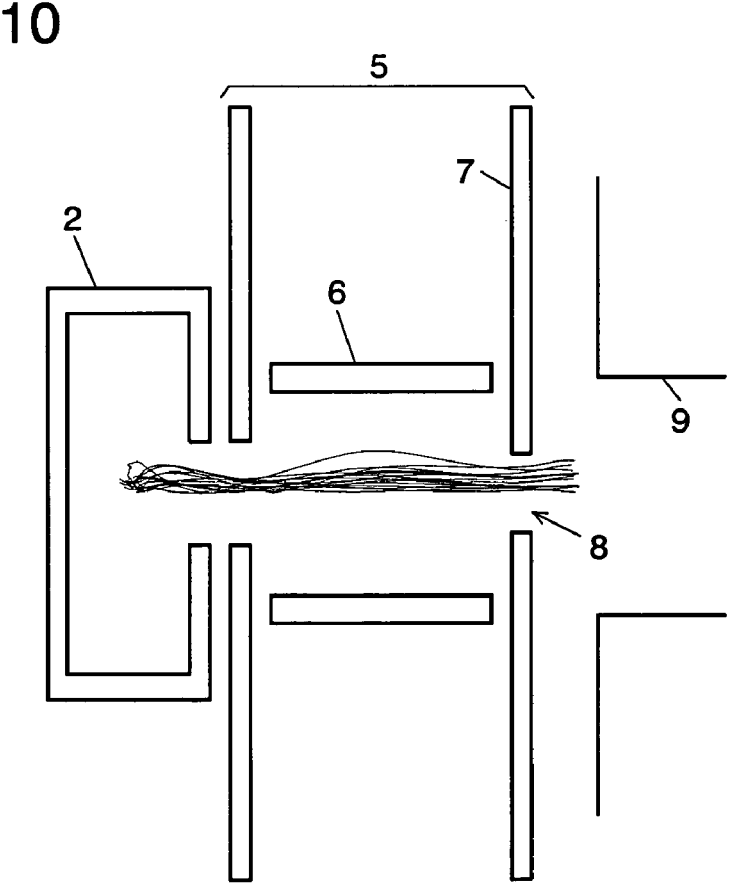
FIG. 10 is a graph of ion trajectories passing through a static electric field of the deflecting electrodes.

A computer simulation is made to confirm the helium ion eliminating effect of the deflecting electrodes 6 as shown in FIG. 2. FIG. 10 is a graph of calculated trajectories of helium ions when a DC voltage is applied to the deflecting electrodes 6 and a static electric field is generated in the space surrounded by them, which shows that most ions pass through the aperture 8.

Figure 11:
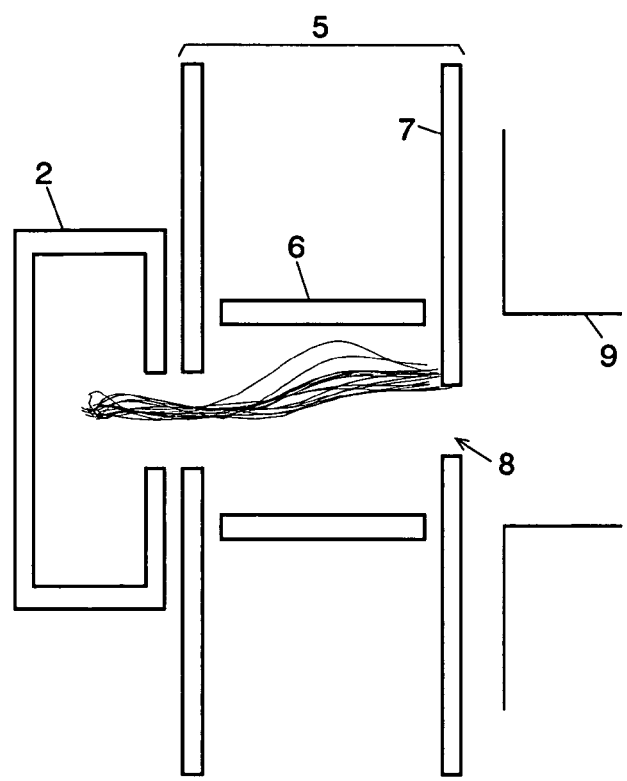
FIG. 11 is a graph of trajectories of helium ions passing through the deflecting electrodes when a DC plus AC voltage is applied to them.

FIG. 11 is a graph of calculated trajectories of helium ions when DC plus AC voltages are applied to the deflecting electrodes 6, which shows that most ions are deflected and collide with the rear end electrode 7. Thus only a few ions can pass through the aperture 8 and enter the quadrupole mass filter 9, and the elimination is effectively achieved.

Figure 12:
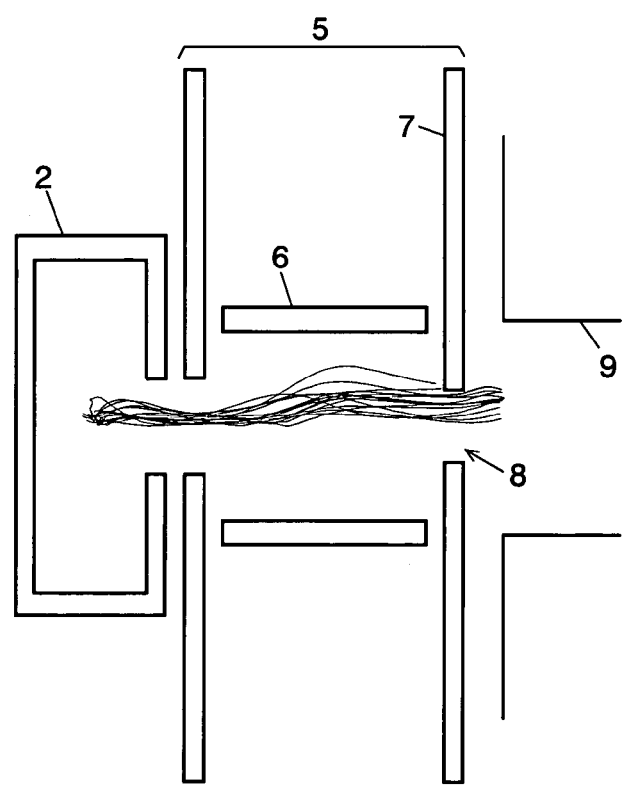
FIG. 12 is a graph of trajectories of ions whose value of the mass to charge ration is 10 passing through the deflecting electrodes when a DC plus AC voltage is applied to them.

FIG. 12 is a graph of calculated trajectories of ions having the mass to charge ratio of 10, which is heavier than helium ions, in the same electric field as that of FIG. 11. In this case, despite the deflecting electric field, most ions pass through the aperture 8 and enter the quadrupole mass filter 9.

The results of the two calculations of FIGS. 10 and 11 show that ions of mass to charge ratio 10 can be mass analyzed with high sensitivity using the deflecting electrodes 6. In summary, owing to the mass spectrometer of the present invention, lighter ions such as helium ions (and actually hydrogen ions) can be adequately prevented, and heavier sample ions can be mass analyzed appropriately.

Although only some exemplary embodiments of the present invention have been described in detail above, those skilled in the art will readily appreciate that many modifications are possible without materially departing from the spirit of the present invention. Accordingly, all such modifications are intended to be included within the scope of this invention. For example, though the deflecting electrodes are placed before the quadrupole mass filter in the above embodiments, they can be placed after the quadrupole mass filter and before the ion detector to prevent carrier helium ions from entering it. The mass separator may not necessarily be the quadrupole mass separator, of course.

What is claimed is:

1. A mass spectrometer comprising:
   an ion source;
   a mass separator for separating ions with respect to mass to charge ratios of the ions;
   an ion detector;
   an ion deflector including a pair of electrodes placed opposite each other across an ion optical axis, the ion deflector being placed between the ion source and the mass separator or between the mass separator and the ion detector; and
   a voltage generator for applying AC voltages of opposite polarities respectively to the pair of electrodes, where a frequency of the AC voltages is determined so that lighter ions are more deflected and prevented from entering the mass separator or the ion detector and heavier ions are less deflected and allowed to enter the mass separator or the ion detector,
   wherein the frequency of the AC voltages is determined so that a number of cycles of the AC voltages arising in a time period in which lighter ions pass through a space between the deflecting electrode is smaller than one and that arising in a time period in which heavier ions pass through the space between the deflecting electrode is larger than one.

2. The mass spectrometer according to claim 1, wherein the frequency of the AC voltage is determined so that the number of cycles of the AC voltages arising in a time period in which lighter ions pass through the space between the deflecting electrode is smaller than a half.

3. The mass spectrometer according to claim 1, wherein the frequency of the AC voltage is determined so that the number of cycles of the AC voltages arising in a time period in which heavier ions pass through the space between the deflecting electrode is larger than two.

4. The mass spectrometer according to claim 1, wherein the ion deflector includes at least two pairs of electrodes, and AC voltages of a same frequency and different phases are applied to two electrodes of every pair.

5. The mass spectrometer according to claim 1, wherein the lighter ions are helium ions.

* * * * *